United States Patent
Oya

(10) Patent No.: US 9,512,770 B2
(45) Date of Patent: Dec. 6, 2016

(54) SENSOR ELEMENT INCLUDING AN AIR INTRODUCTION PORTION WITH A CROSS SECTION HAVING SPECIFIED ASPECT RATIO AND AREA AND SENSOR INCLUDING THE SAME

(71) Applicant: NGK SPARK PLUG CO., LTD., Nagoya-shi, Aichi (JP)

(72) Inventor: Seiji Oya, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 182 days.

(21) Appl. No.: 14/445,008

(22) Filed: Jul. 28, 2014

(65) Prior Publication Data

US 2015/0040642 A1 Feb. 12, 2015

(30) Foreign Application Priority Data

Aug. 9, 2013 (JP) ................. 2013-166500

(51) Int. Cl.
*G01N 7/00* (2006.01)
*F01N 11/00* (2006.01)
(Continued)

(52) U.S. Cl.
CPC ............. *F01N 11/007* (2013.01); *F02B 37/16* (2013.01); *F02B 37/18* (2013.01);
(Continued)

(58) Field of Classification Search
CPC ............. F02D 41/1454; F02D 41/1456; F02D 41/1495; G01N 27/407; G01N 33/0036; G01N 27/00; Y02T 10/40
(Continued)

(56) References Cited

U.S. PATENT DOCUMENTS

2005/0241937 A1* 11/2005 Shichida ............ G01N 27/4077
204/424
2007/0243760 A1* 10/2007 Fujita ................. G01N 27/4071
439/585
(Continued)

FOREIGN PATENT DOCUMENTS

JP 2005-049115 A 2/2005

*Primary Examiner* — Eric S McCall
*Assistant Examiner* — Mohammed E Keramet-Amircolai
(74) *Attorney, Agent, or Firm* — Stites & Harbison, PLLC; Jeffrey A. Haeberlin; James R. Hayne

(57) ABSTRACT

Disclosed is a sensor element for detecting a specific gas component in a gas under measurement. The sensor element is plate-shaped in a longitudinal direction thereof and has a detection portion located on a front end side of the sensor element and an air introduction portion adapted as a longitudinal hole extending in the longitudinal direction to a position of the detection portion so as to introduce air thereinto. The detection portion includes a measurement electrode exposed to the gas under measurement, a reference electrode arranged in the air introduction portion and a plate-shaped solid electrolyte member held in contact with the measurement electrode and the reference electrode. The air introduction portion has a cross section with an aspect ratio of 0.0082 to 0.0800 and an area of 0.015 to 0.147 mm² when taken perpendicular to the longitudinal direction at a position of the reference electrode.

6 Claims, 4 Drawing Sheets

(51) Int. Cl.
    *G01N 27/407*     (2006.01)
    *F02B 37/16*     (2006.01)
    *F02B 37/18*     (2006.01)

(52) U.S. Cl.
    CPC ..... *G01N 27/4071* (2013.01); *G01N 27/4077* (2013.01); *F01N 2560/02* (2013.01); *F01N 2560/20* (2013.01); *Y02T 10/144* (2013.01)

(58) Field of Classification Search
    USPC .................................................. 73/23.32
    See application file for complete search history.

(56) References Cited

U.S. PATENT DOCUMENTS

| | | | | |
|---|---|---|---|---|
| 2007/0251823 | A1* | 11/2007 | Yamada | G01N 27/4077 204/424 |
| 2008/0067066 | A1* | 3/2008 | Okumura | G01N 27/4077 204/424 |
| 2008/0067067 | A1* | 3/2008 | Oya | G01N 27/419 204/426 |
| 2008/0073209 | A1* | 3/2008 | Yamada | G01N 27/4071 204/424 |
| 2008/0121020 | A1* | 5/2008 | Oya | G01N 27/4071 73/31.05 |
| 2010/0243444 | A1* | 9/2010 | Wakazono | G01N 27/419 204/412 |
| 2010/0264027 | A1* | 10/2010 | Nakagawa | G01N 27/4071 204/431 |
| 2012/0118039 | A1* | 5/2012 | Tsuzuki | G01N 27/4077 73/23.2 |

\* cited by examiner

SENSOR ELEMENT INCLUDING AN AIR INTRODUCTION PORTION WITH A CROSS SECTION HAVING SPECIFIED ASPECT RATIO AND AREA AND SENSOR INCLUDING THE SAME

BACKGROUND OF THE INVENTION

The present invention relates to a sensor element for detecting a specific gas component in a gas under measurement and a sensor equipped with such an sensor element.

As an example of a sensor having a sensor element for detecting a specific gas component in a gas under measurement, conventionally known is an oxygen sensor for use in an exhaust system of an internal combustion engine to measure the concentration of oxygen in an exhaust gas for combustion control of the internal combustion engine. This oxygen sensor has, for example, a cylindrical metal shell and a plate-shaped sensor element held in the metal shell.

Japanese Laid-Open Patent Publication No. 2005-049115 (hereinafter abbreviated as "JP2005-049115A") discloses one type of sensor element that includes a detection portion located on a front side in a longitudinal direction thereof and an air introduction portion adapted to introduce air thereinto. The detection portion has a measurement electrode exposed to a gas under measurement, a reference electrode arranged in the air introduction portion and a plate-shaped solid electrolyte member held in contact with both of the measurement electrode and the reference electrode. Upon contact of the gas under measurement with the measurement electrode and contact of the air with the reference electrode, the sensor element generates an electromotive force between the measurement electrode and the reference electrode via the solid electrolyte member according to a ratio between the concentrations of a specific gas component (oxygen) in the gas under measurement and in the air. The thus-generated electromotive force can be used as a gas detection signal for detection of the specific gas component.

The sensor element is shifted to an activated state capable of detecting the specific gas component when the solid electrolyte member is heated to an activation temperature by a heater. In particular, the sensor element of JP2005-049115A shows good gas responsivity, rapid temperature rise by the heater and high durability against repeated rapid temperature rises.

SUMMARY OF THE INVENTION

The above conventional sensor element enables rapid temperature rise by the heater. However, the overall heat capacity of the sensor element is increased to cause a deterioration of thermal conduction efficiency when the air introduction portion is relatively large in the sensor element. This results in a large power consumption of the heater for rapid temperature rise of the sensor element.

As a solution to such a problem, it is conceivable to decrease the size of the air introduction portion in the sensor element. If the air introduction portion is excessively decreased, however, there arises a possibility that the air introduction portion may fail to provide a sufficient air supply to the reference electrode of the detection portion.

In view of the foregoing, it is an object of the present invention to provide a sensor element with a detection portion and an air introduction portion so as to prevent an insufficient air supply from the air introduction portion to a reference electrode of the detection portion while reducing the power consumed by a heater for heating of the sensor element. It is also an object of the present invention to provide a sensor with such a sensor element.

According to one aspect of the present invention, there is provided a sensor element for detecting a specific gas component in a gas under measurement, the sensor element having a plate shape extending in a longitudinal direction thereof and comprising: a detection portion located on a front end side of the sensor element; and an air introduction portion adapted as a longitudinal hole having an opening and extending in the longitudinal direction from the opening to a position of the detection portion so as to introduce air thereinto through the opening, the detection portion including a measurement electrode exposed to the gas under measurement, a reference electrode arranged in the air introduction portion and a plate-shaped solid electrolyte member held in contact with both of the measurement electrode and the reference electrode, wherein a cross section of the air introduction portion taken perpendicular to the longitudinal direction at a position of the reference electrode has an aspect ratio of 0.0082 to 0.0800 and an area of 0.015 to 0.147 $mm^2$. (The cross section of the air introduction portion taken perpendicular to the longitudinal direction at the position of the reference electrode is hereinafter also simply referred to as the "cross section" of the air introduction portion.)

As is apparent from comparison of the after-mentioned test results of Example 3 and Comparative Example 3 in TABLE 1, the sensor element can prevent an increase in overall heat capacity and obtain improvement in thermal conduction efficiency so as to reduce the power consumption required for heating of the sensor element when the area of the cross section of the air introduction portion is 0.147 $mm^2$ or smaller. The sensor element can also prevent an increase in overall heat capacity and obtain improvement in thermal conduction efficiency so as to reduce the power consumption required for heating of the sensor element when the aspect ratio of the cross section of the air introduction portion is 0.0800 or smaller as is apparent from comparison of the after-mentioned test results of Example 9 and Comparative Example 1 in TABLE 1.

Further, the sensor element can introduce a sufficient amount of air from the air introduction portion and prevent an insufficient air supply to the reference electrode when the area of the cross section of the air introduction portion is 0.015 $mm^2$ or larger as is apparent from comparison of the after-mentioned test results of Example 7 and Comparative Example 4 in TABLE 1. As is apparent from comparison of the after-mentioned test results of Example 1 and Comparative Example 2 in TABLE 1, the sensor element can also introduce a sufficient amount of air from the air introduction portion and prevent an insufficient air supply to the reference electrode when the aspect ratio of the cross section of the air introduction portion is 0.0082 or larger.

Namely, it is possible to not only reduce the power consumption required for heating of the sensor element but also prevent the insufficient air supply to the reference electrode by controlling the aspect ratio and area of the cross section of the air introduction portion to within the above specific ranges. The sensor element of the present invention is therefore able to provide a sufficient air supply from the air introduction portion to the reference electrode of the detection portion while reducing the power consumption for heating of the sensor element.

In the present invention, it is preferable that the cross section of the sensor element has a height dimension of 0.015 to 0.080 mm in a direction perpendicular to a plate surface of the solid electrolyte member.

As is apparent from comparison of the after-mentioned test results of Examples 3, 6 and 9 and Comparative Example 1 in TABLE 1, the sensor element can prevent an increase in overall heat capacity and obtain improvement in thermal conduction efficiency so as to reduce the power consumption required for heating of the sensor element when the height dimension of the cross section of the air introduction portion is 0.080 mm or smaller.

The sensor element can introduce a sufficient amount of air from the air introduction portion and prevent an insufficient air supply to the reference electrode when the height dimension of the cross section of the air introduction portion is 0.015 mm or larger as is apparent from the after-mentioned test results of Examples 1, 4 and 7 in TABLE 1.

It is namely possible to reduce the power consumption required for heating of the sensor element and prevent the insufficient air supply to the reference electrode by controlling the height dimension of the cross section of the air introduction portion to within the above specific range. Thus, the sensor element of the present invention is able to provide a sufficient air supply to the reference electrode of the detection portion while reducing the power consumption for heating of the sensor element.

It is further preferable in the present invention that a cross section of the sensor element taken perpendicular to the longitudinal direction at a position of the detection portion has an aspect ratio of 0.111 to 0.400 and an area of 0.80 to 4.32 $mm^2$. (The cross section of the sensor element taken perpendicular to the longitudinal direction at the position of the detection portion is hereinafter also simply referred to as the "cross section" of the sensor element.)

As is apparent from comparison of the after-mentioned test results of Example 11 and Comparative Example 11 in TABLE 2, the sensor element can prevent an increase in overall heat capacity and obtain improvement in thermal conduction efficiency so as to reduce the power consumption required for heating of the sensor element when the area of the cross section of the sensor element is 4.32 $mm^2$ or smaller. The sensor element can also prevent an increase in overall heat capacity and obtain improvement in thermal conduction efficiency so as to reduce the power consumption required for heating of the sensor element when the aspect ratio of the cross section of the sensor element is 0.400 or smaller as is apparent from comparison of the after-mentioned test results of Examples 17 and 20 and Comparative Example 14 in TABLE 2.

Further, the sensor element can secure its strength and be prevented from breakage when the area of the cross section of the sensor element is 0.80 $mm^2$ or larger as is apparent from comparison of the after-mentioned test results of Example 21 and Comparative Example 15 in TABLE 2. As is apparent from comparison of the after-mentioned test results of Example 13 and Comparative Example 13 in TABLE 2, the sensor element can also its strength and be prevented from breakage when the aspect ratio of the cross section of the sensor element is 0.111 or larger.

Namely, it is possible to reduce the power consumption required for heating of the sensor element and ensure the strength of the sensor element for prevention of breakage of the sensor element by controlling the aspect ratio and area of the cross section of the sensor element to within the above specific ranges. The sensor element is therefore able to ensure its strength and prevent breakage while reducing the power consumption for heating of the sensor element.

In addition to the above configuration, it is preferable that the cross section of the sensor element has a width dimension of 2.0 to 3.6 in a direction parallel to a plate surface of the sensor element.

As is apparent from comparison of the after-mentioned test results of Examples 11, 12 and 13 and Comparative Example 11 and 12 in TABLE 2, the sensor element can prevent an increase in overall heat capacity and obtain improvement in thermal conduction efficiency so as to reduce the power consumption required for heating of the sensor element when the width dimension of the cross section of the sensor element is 3.6 mm or smaller.

The sensor element can secure its strength and be prevented from breakage when the width dimension of the cross section of the sensor element is 2.0 $mm^2$ or larger as is apparent from the after-mentioned test results of Examples 20 and 21 in TABLE 2.

It is namely possible to reduce the power consumption required for heating of the sensor element and ensure the strength of the sensor element for prevention of breakage of the sensor element by controlling the width dimension of the cross section of the sensor element to within the above specific range. The sensor element of the present invention is thus able to ensure its strength and prevent breakage while reducing the power consumption for heating of the sensor element.

Furthermore, it is preferable that a height dimension of the reference electrode in a direction perpendicular to a plate surface of the solid electrolyte member is 0.002 mm or larger and is smaller than or equal to a value of subtraction of 0.005 mm from the height dimension of the cross section of the air introduction portion.

When the height dimension of the reference electrode is smaller than or equal to the value of subtraction of 0.005 mm from the height dimension of the cross section of the air introduction portion, the sensor element can secure a clearance between the reference electrode and an inner surface of the air introduction portion facing the reference electrode so as to secure a large area of contact between the reference electrode and the air and provide the reference electrode with reliable sensitivity to the specific gas component in the air.

When the height dimension of the reference electrode is 0.002 mm or larger, the sensor element can secure the volume of the reference electrode required for reaction with the specific gas component and permit the proper function of the reference electrode so as to generate the electromotive force between the measurement electrode and the reference electrode.

The sensor element of the present invention is thus able to ensure the large area of contact between the reference electrode and the air and properly generate the electromotive force between the measurement electrode and the reference electrode according to the concentration ratio of the specific gas component by controlling the height dimension of the reference electrode to within the above specific range.

According to another aspect of the present invention, there is provided a sensor with the above-mentioned sensor element.

By the adoption of the above-mentioned sensor element, the sensor of the present invention is able to the same effects as those mentioned above.

In this way, it is possible in the present invention to provide a sufficient air supply to the reference electrode of the detection portion while reducing the power consumption required for heating of the sensor element.

The other objects and features of the present invention will also become understood from the following description.

DESCRIPTION OF THE EMBODIMENTS

The present invention will be described below with reference to the drawings. The following embodiment specifically refers to, as one type of oxygen gas sensor, an air-fuel ratio sensor 1 mounted to an exhaust pipe of an internal combustion engine in an automotive vehicle etc. to measure a specific gas component (oxygen) in an exhaust gas under measurement (hereinafter simply referred to as "exhaust gas") for air-fuel ratio feedback control of the internal combustion engine.

1. Embodiment 1-1. Overall Structure of Gas Sensor

Figure 1:
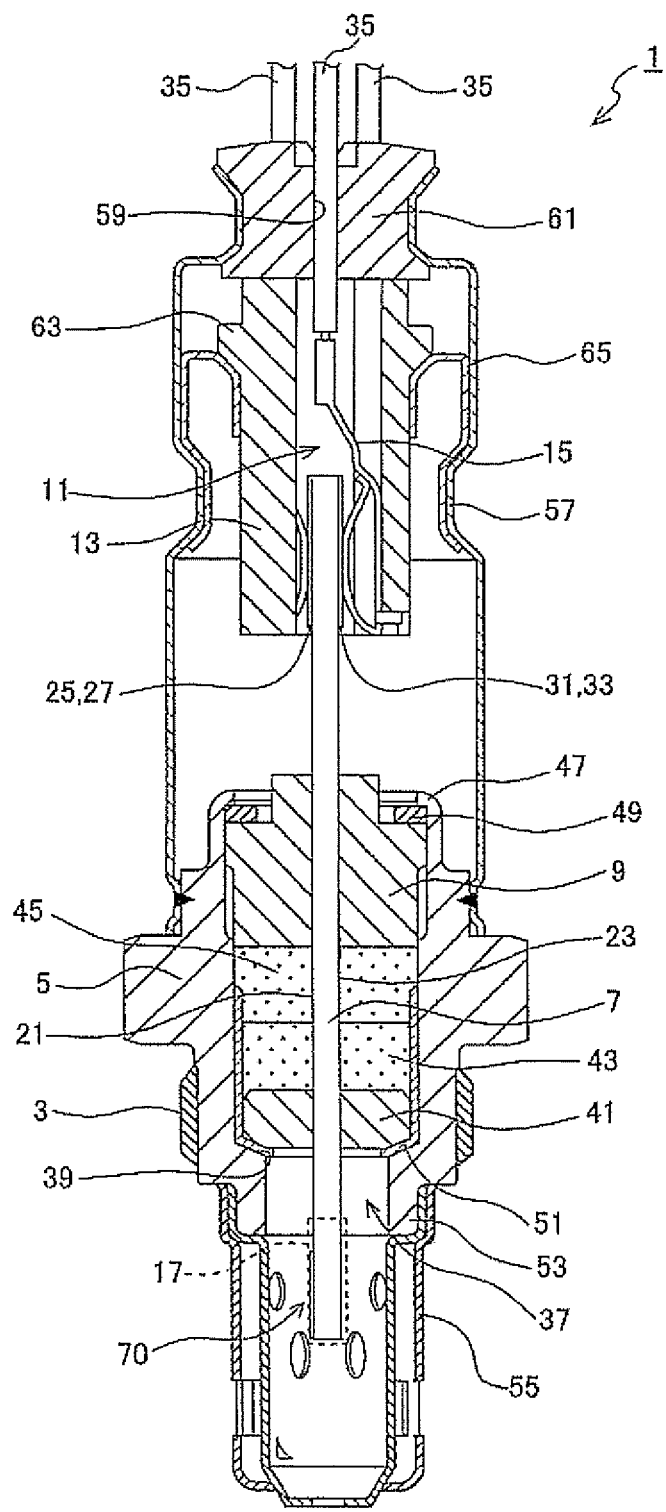
FIG. 1 is a cross-sectional internal view of an air-fuel ratio sensor with a sensor element according to one embodiment of the present invention.

The overall structure of the air-fuel ratio sensor 1 will be first explained below with reference to FIG. 1. FIG. 1 is a cross-sectional internal view of the air-fuel ratio sensor 1.

As shown in FIG. 1, the air-fuel ratio sensor 1 includes a cylindrical metal shell 5 having a thread portion 5 formed on an outer circumferential surface thereof for mounting to the exhaust pipe, a plate-shaped gas sensor element 7 extending in an axial direction of the air-fuel ratio sensor 1 (longitudinal direction; vertical direction in FIG. 1), a cylindrical ceramic sleeve 9 surrounding a radial outer circumference of the gas sensor element 7, an insulating contact member (separator) 13 having an insertion hole 11 formed therethrough in the axial direction so as to circumferentially surround a rear end part of the gas sensor element 7 by an inner wall surface of the insertion hole 11 and a plurality of connection terminals 15 (only two are shown in FIG. 1) arranged between the gas sensor element 7 and the separator 13. A plurality of leads 35 (five leads 35 in the present embodiment; only three are shown in FIG. 1) are provided for connection of the air-fuel ratio sensor 1 to external equipment.

As will be explained later in detail, the gas sensor element 7 has a plate-shaped sensor element body 71 (also referred to as "oxygen pumping cell") extending in a longitudinal direction thereof (horizontal direction in FIG. 2), a plate-shaped heater 73 laminated on the sensor element body 71 and extending in the longitudinal direction and a protection layer 17 covering front end parts (left side in FIG. 2) of the sensor element body 71 and the heater 73. Herein, the front end parts of the sensor element body 71 and the heater 73 constitute a detection portion 70 of the air-fuel ratio sensor 1, which is exposed to the exhaust gas. The gas sensor element 7 also has, at its rear side (upper side in FIG. 1), electrode pads 25, 27, 31 and 33 arranged on opposite outer surfaces i.e. first and second main surfaces 21 and 23 thereof (see FIGS. 2 and 3 mentioned later).

The connection terminals 15 are electrically connected to the respective electrode pads 25, 27, 31 and 33 of the gas sensor element 7 and to the respective leads 35 so as to establish a current flow path between the gas sensor element 7 (electrode pads 25, 27, 31 and 33) and the external equipment.

The metal shell 5 is substantially cylindrical in shape with a through hole 37 formed therethrough in the axial direction and a radially inwardly protruding step portion 39 formed in the through hole 37. The gas sensor element 7 is inserted and held in the through hole 37 of the metal shell 5 such that a gas introduction region 322 (see FIG. 4) of the detection portion 70 is located front of a front end of the through hole 37 and such that the electrode pads 25, 27, 31 and 33 are located rear of a rear end of the through hole 37.

An annular ceramic holder 41, talc rings 43 and 45 and the ceramic sleeve 9 are stacked together in order of mention from the front side to the rear side within the through hole 37 of the metal shell 5 so as to surround the radial outer circumference of the gas sensor element 7.

A crimp packing 49 is disposed between the ceramic sleeve 9 and a rear end portion 47 of the metal shell 5. A metal holder 51 is disposed between the ceramic holder 41 and the step portion 39 of the metal shell 5 so as to hold therein the talc ring 43 and the ceramic holder 41. The rear end portion 47 of the metal shell 5 is crimped onto the ceramic sleeve 9 via the crimp packing 49 in a direction that pushes the ceramic sleeve 9 toward the front.

A protector 55 is attached to an outer circumference of a front end portion 53 of the metal shell 5 by e.g. welding so as to cover the protruding front end part of the gas sensor element 7. In the present embodiment, the protector 55 has a double-layer structure of metal (such as stainless steel).

On the other hand, an outer tube 57 is attached to an outer circumference of a rear side portion of the metal shell 5. A grommet 61 is fitted in a rear opening of the outer tube 57. Lead insertion holes 59 are formed in the grommet 61 such that the leads 35 are inserted through the lead insertion holes 59 and drawn out of the air-fuel ratio sensor 1.

A protruding portion 63 is formed on an outer circumference of the separator 13 and fixed to the outer tube 57 by a holding member 65.

1-2. Structure of Sensor Element

Figure 2:
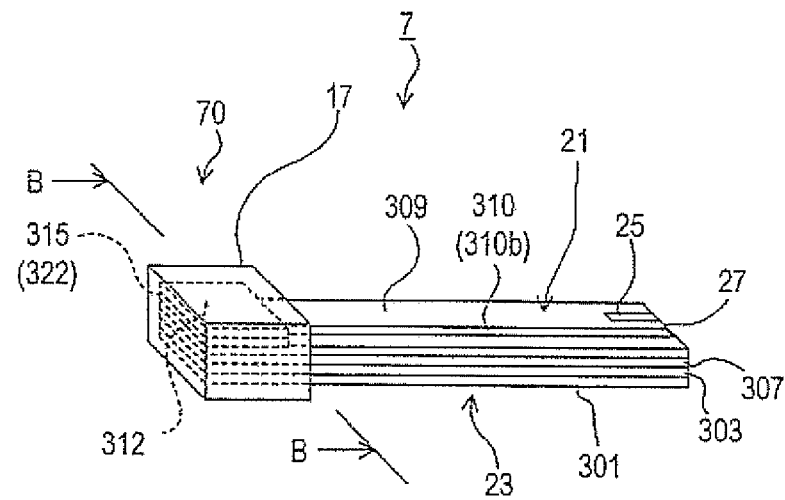
FIGS. 2 and 3 is an external perspective view and an exploded perspective view of the sensor element, respectively.
Figure 3:
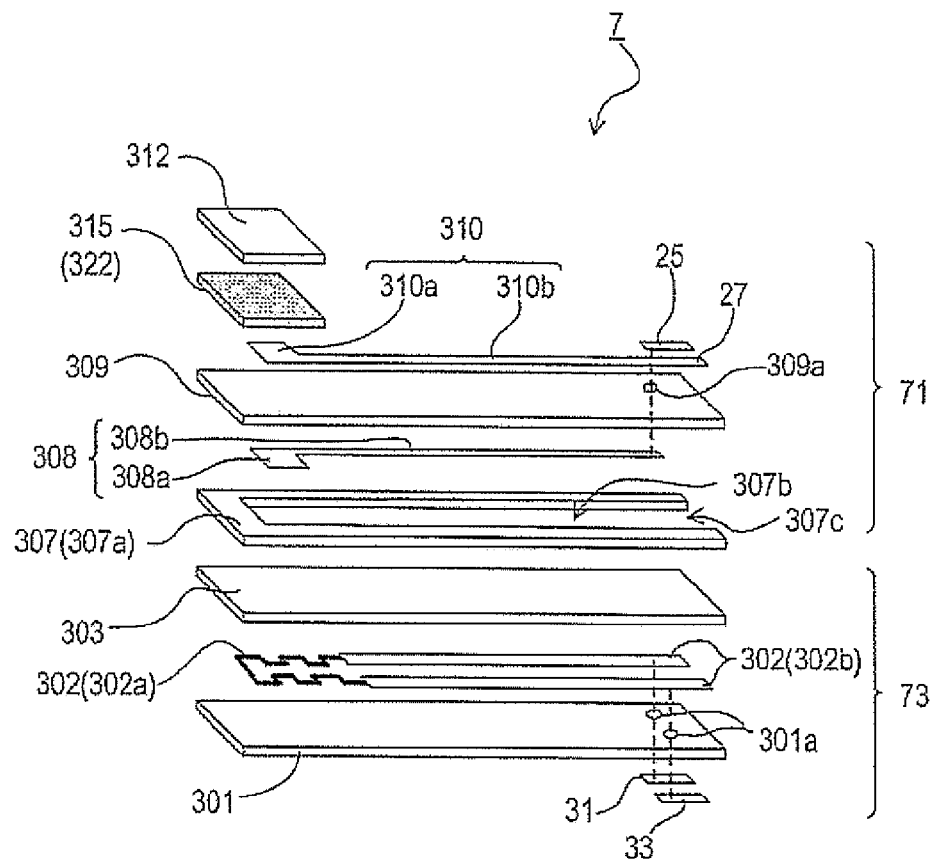
Figure 4:
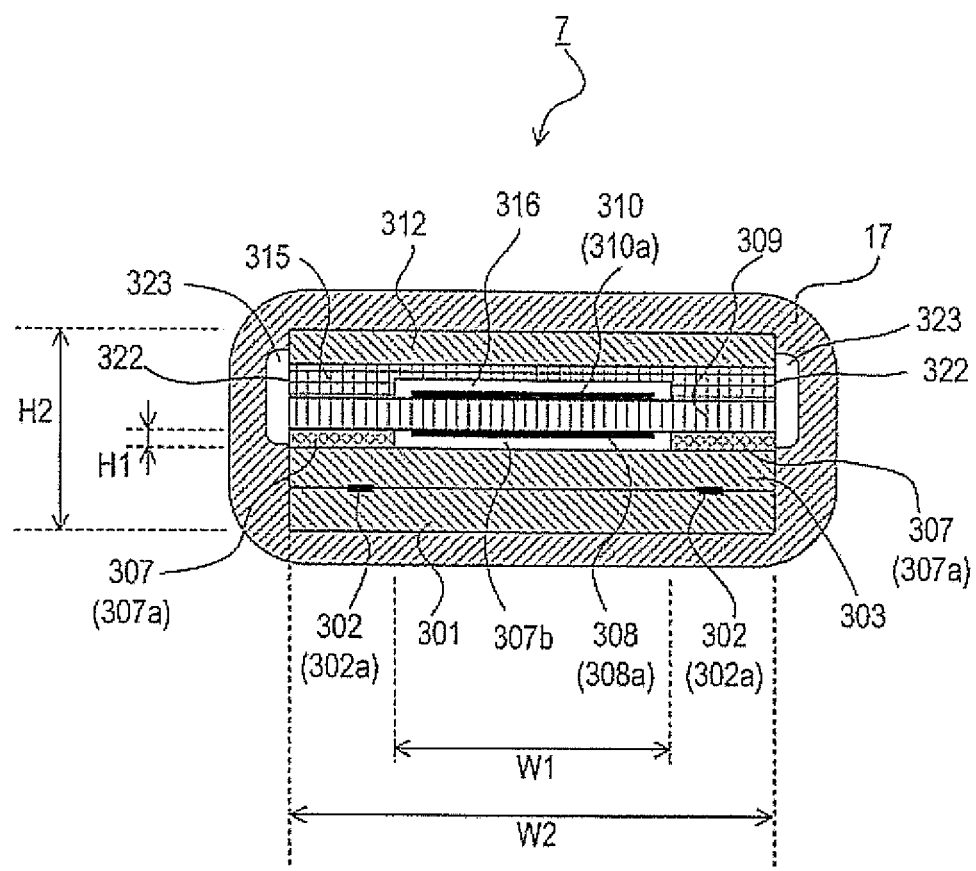
FIG. 4 is an end view of the sensor element as viewed along line B-B of FIG. 2.

Next, the structure of the gas sensor element 7 will be explained below with reference to FIGS. 2 to 4. FIG. 2 is an external perspective view of the gas sensor element 7; FIG. 3 is an exploded perspective view of the gas sensor element 7; and FIG. 4 is an end view of the gas sensor element 7 as viewed along line B-B of FIG. 2. It is noted that: the structures of the sensor element body 71 and the heater 73 inside the protection layer 17 are indicated by dotted lines in FIG. 2; and the protection layer 17 is omitted from FIG. 3 for purposes of illustrations.

As shown in FIG. 2 and as mentioned above, the gas sensor element 7 is equipped with the plate-shaped sensor element body 71 (oxygen pumping cell 71), the plate-shaped heater 73 and the protection layer 17. The detection portion 70 of the gas sensor element 7 is constituted by the front end parts of the sensor element body 71 and the heater 73. As shown in FIG. 4, the gas introduction region 322 is formed in the detection portion 70 for introduction of the exhaust gas. Further, the detection portion 70 has formed therein a gas measurement chamber 316 into which the exhaust gas is introduced through the gas introduction region 322.

More specifically, the gas sensor element 7 has a laminated structure in which a shielding layer 312, a diffusion limiting member 315, the sensor element body 71, an insulating layer 307 and the heater 73 are laminated together as shown in FIG. 3.

The heater 73 has first and second substrates 301 and 303 predominantly made of alumina and a heater element 302 predominantly made of platinum and sandwiched between the first and second substrates 301 and 303. The heater element 302 includes a heater region 302a located on a front end side thereof and a pair of heater lead regions 302b extending from the heater region 302a in a longitudinal direction of the first substrate 301. Heater-side through holes 301a are formed in the first substrate 301 such that terminal ends of the heater lead regions 302b are electrically connected to the electrode pads 31 and 32 through the heater-side through holes 301a.

The sensor element body 71 has a first solid electrolyte member 309 and first and second electrodes 308 and 310 formed on opposite surfaces of the first solid electrolyte member 309. The first electrode 308 includes a first electrode region 308a and a first lead region 308b extending from the first electrode region 308a in a longitudinal direction of the first solid electrolyte member 309. The second electrode 310 includes a second electrode region 310a and a second lead region 310b extending from the second electrode region 310a in the longitudinal direction of the first solid electrolyte member 309. A first through hole 309a is formed in the first solid electrolyte member 309 such that a terminal end of the first lead region 308b is electrically connected to the electrode pad 25. A terminal end of the second lead region 310b is formed integral with the terminal pad 27.

The first solid electrolyte member 309 is made of a sintered partially stabilized zirconia in which yttria ($Y_2O_3$) or calcia (CaO) is added as a stabilizer to zirconia ($ZrO_2$).

The heater element 302, the first and second electrodes 308 and 310 and the electrode pads 25, 27, 31 and 33 are each made of a platinum group element. Suitable examples of the platinum group element are Pt, Ph and Pd. These elements can be used solely or in combination of two or more thereof.

The insulating layer 307 is arranged between the sensor element body 71 and the heater 73 and provided with an insulation portion 307a and an air introduction portion 307b. There is no particular limitation on the material of the insulating layer 307 as long as the insulating layer 307 is made of a sintered insulating ceramic material. For example, an oxide ceramic material such as alumina or mullite can be used as the material of the insulating layer 307.

The air introduction portion 307b is adapted as a slot (elongated hole) having an opening 307c on a rear end side of the insulating layer 307 and extending in the longitudinal direction from the opening 307 to a position of the detection portion 70 (more specifically, the first electrode region 308a). The air introduction portion 307b is in communication with the outside through the opening 307c so as to introduce the air thereinto. As shown in FIG. 4, the air introduction portion 307b has a rectangular cross section when taken perpendicular to the longitudinal direction at the position of the first electrode region 308a. (The cross section of the air introduction portion 307b taken perpendicular to the longitudinal direction at the position of the first electrode region 308a is also simply referred to as the "cross section" of the air introduction portion 307b as already mentioned before.) Herein, the cross section of the air introduction portion 307b refers to a region surrounded by the second substrate 303, the insulation portion 307a and the first solid electrolyte member 309 and including the first electrode region 308a.

The gas measurement chamber 316 is situated on the surface of the first solid electrolyte member 309 so as to cover the second electrode region 310a of the second electrode 310 and is covered by the diffusion limiting member 315. The shielding layer 312 is arranged on a surface of the diffusion limiting member 315 opposite from the first solid electrolyte member 309.

The diffusion limiting member 315 is made of a porous alumina material. Four lateral sides of the diffusion limiting member 315, which are not in contact with the shielding layer 312 and the first solid electrolyte member 309, are exposed to the after-mentioned hollow space 323. These exposed sides of the diffusion limiting member 315 serve as the gas introduction region 322 of the detection portion 70. In other words, the gas introduction region 322 of the detection portion 70 is directed to four different directions.

The protection layer 17 is made of a porous alumina material having lower diffusion resistance than that of the diffusion limiting member 315 and is located outside the shielding layer 312 and the gas introduction region 322 (diffusion limiting member 315) of the detection portion 70. In the present embodiment, the protection layer 17 is formed so as to cover the gas introduction region 322 while being kept separated from the diffusion limiting member 315. More specifically, the hollow space 323 is made in an inner surface of the protection layer 17 facing the gas introduction region 322 of the detection portion 70. The hollow space 323 is thus located between the protection layer 17 and the diffusion limiting member 315 such that the protection layer 17 and the diffusion limiting member are kept separated from each other by the hollow space 323.

Accordingly, the gas sensor element 7 is so structured that the exhaust gas flows to the gas introduction region 322 through the protection layer 17 and the hollow space 323, and then, gets introduced into the gas measurement chamber 316 through the diffusion limiting member 315. As mentioned above, the protection layer 17 and the diffusion limiting member 315 are kept separated from each other in the presence of the hollow space 323 between the protection layer 17 and the diffusion limiting member 315. This allows, even when water is adhered to the protection layer 17, prevention of such adhered water from penetrating into the diffusion limiting member 315 by the so-called capillary action.

1-3. Manufacturing Process of Gas Sensor

A manufacturing process of the air-fuel ratio sensor 1 will be next explained below.

The gas sensor element 7 is produced by the following procedure.

Various lamination materials for production of the gas sensor element 7, such as a solid electrolyte green sheet for the first solid electrolyte member 309 of the sensor element body 71, insulating green sheets for the insulation portion 307a of the insulating layer 307 and for the first and second substrates 301 and 303 of the heater 73 and the like, are first laminated together. The thus-obtained uncompressed laminate is provided with green electrode pad materials for the electrode pads 25, 27, 31 and 33 etc.

For example, the solid electrolyte green sheet can be prepared by mixing a ceramic powder predominantly composed of zirconia, an alumina powder and a butyral resin together, adding a mixed solvent (toluene and methyl ethyl ketone) to the powder mixture, forming the resulting slurry into a sheet shape by a doctor blade method, and then, evaporating the mixed solvent from the sheet.

The insulating green sheet can be prepared by mixing a ceramic material predominantly composed of alumina, a butyral resin and dibutyl phthalate together, adding a mixed solvent (toluene and methyl ethyl ketone) to the powder mixture, forming the resulting slurry into a sheet shape by a doctor blade method, and then, evaporating the mixed solvent from the sheet.

In the case where the height (thickness) dimension of the insulation portion 307a of the insulating layer 307 is set to a small value, the preparation method of the insulating green sheet is not limited to the doctor blade method. It is feasible to adopt a screen printing method etc. in place of the doctor blade method. In other words, the slurry can be formed into a sheet of smaller thickness by the screen printing method than by the doctor plate method.

An insert material capable of subliming or burning off by firing (e.g. paste predominantly composed of carbon) is arranged in the region to be hollowed out by firing (such as the air introduction portion 307b).

Further, the green diffusion limiting member can be prepared by dispersing 100 mass % of alumina powder and a plasticizer (butyral resin and DBP) together by a wet mixing method and applying the resulting slurry to the region to be formed into the diffusion limiting member 315 by firing.

Figure 5:
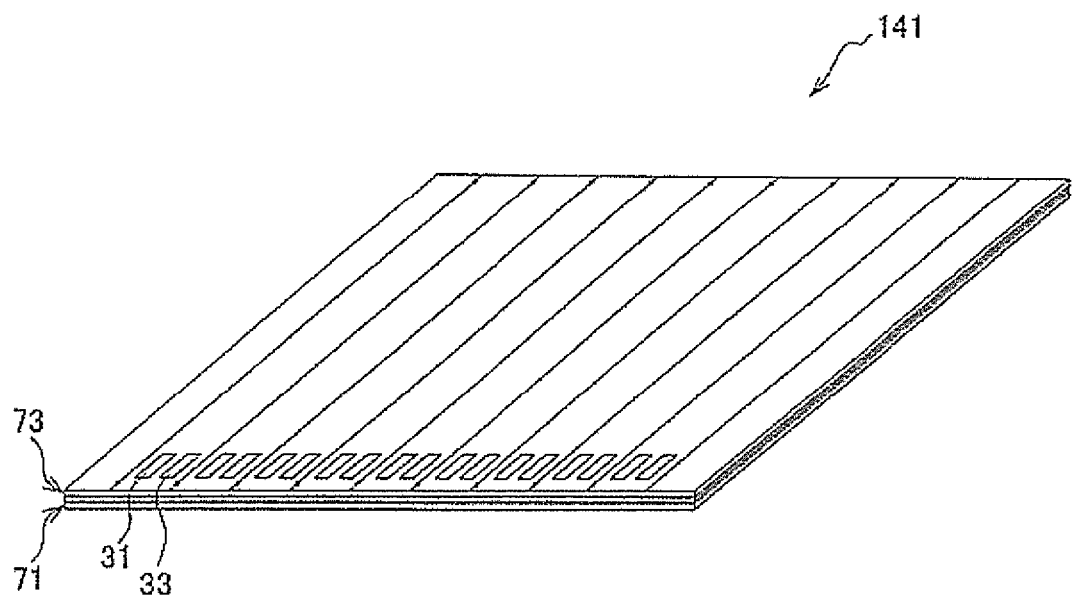
FIG. 5 is a schematic view of a laminated base material for production of the sensor element.

The above uncompressed laminate is pressurized at 1 MP, thereby obtaining a compressed laminate material 141 as shown in FIG. 5 as a base material of the gas sensor element 7. It is noted that FIG. 5 shows the outward appearance of the laminate material 141 (the base material of the gas sensor element 7) as viewed from the heater side rather than the heater element body side.

The laminate material 141 is cut into a plurality of (e.g. ten) green laminate pieces of predetermined size such that the green laminate pieces each substantially agree in size with the sensor element body 71 and the heater 73 of the gas sensor element 7.

Figure 6:
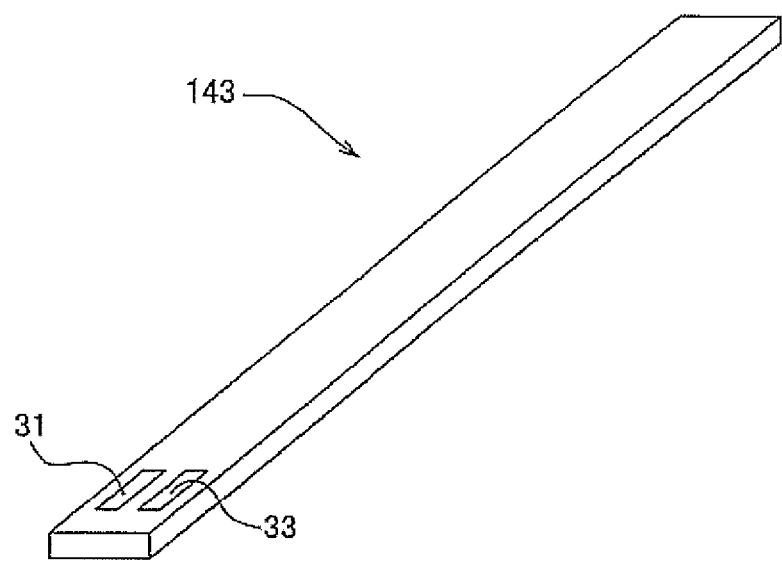
FIG. 6 is a schematic view a semifinished product of the sensor element.

Each of these green laminate pieces is subjected to resin removal and main firing at 1500° C., thereby obtaining a fired laminate product 143 as shown in FIG. 6 as a semi-finished product of the gas sensor element 7 in which the sensor element body 71 and the heater 73 are laminated together.

The laminate product 143 is subjected to trimming such that the diffusion resistance (diffusion limiting performance) of the diffusion limiting member 315 is controlled to a predetermined target value. The trimming can be done by e.g. applying a trimming liquid to the porous portion or cutting the porous portion.

Subsequently, a green protection layer is formed around a front end part of the laminate product 143 by printing a paste predominantly composed of carbon around the gas introduction region 322 at which the diffusion limiting member 315 is exposed, i.e., on the region to be formed into the hollow space 323 by firing, preparing a slurry of spinel powder, titania and alumina sol, and then, spraying or applying the slurry onto the entire circumference of the front end part of the laminate product 143.

The laminated product 143 with the green protection layer is subjected to heat treatment under the conditions of a firing temperature of 1000° C. and a firing time of 3 hours so as to form the protection layer 17 with the hollow space 323 by burning off of the carbon paste. With this, the gas sensor element 7 is obtained.

Then, the gas sensor element 7 and the metal shell 5 are assembled together by inserting the gas sensor element 7 into the metal holder 51, securing the gas sensor element 7 with the ceramic holder 41 and the talc ring 43, fixing the resulting subassembly in the metal shell 51 and fitting the talc ring 45 and the ceramic sleeve 9 around the rear end portion of the gas sensor element 7 and into the metal shell 5.

After that, a lower assembly unit is formed by crimping the rear end portion 47 of the metal shell 5 onto the ceramic sleeve 9 and attaching the protector 55 to the front end portion 53 of the metal shell 5. On the other hand, an upper assembly unit is formed by assembling the outer tube 57, the separator 13, the grommet 61 etc. together.

The air-fuel ratio sensor 1 is completed by joining the upper and lower assembly units to each other.

1-4. Measurement Test

The following measurement tests were conducted in order to verify the effects of control of the cross section of the air introduction portion 307b, the cross section of the gas sensor element 7 and the height (thickness) dimension of the first electrode region 308a on the sensor performance (heater power consumption and air flow amount).

(Measurement Test 1)

The gas sensor element 7 was tested for the heater power consumption and air flow amount by varying the cross section of the air introduction portion 307b. As mentioned before, the cross section of the air introduction portion 307b refers to that taken perpendicular to the longitudinal direction at the position of the first electrode region 308a.

In Measurement Test 1, nine types of sensor element samples as Examples 1 to 9 of the present invention and four types of sensor element samples as Comparative Examples 1 to 4 were prepared. The thickness (height) and width dimensions, aspect ratio and area of the cross section of the air introduction portion 307b of the respective sensor element samples are indicated in TABLE 1.

TABLE 1

| | Air introduction hole | | | | | |
|---|---|---|---|---|---|---|
| | Thickness (mm) | Width (mm) | Aspect ratio | Cross-sectional area ($mm^2$) | Heater power consumption | Air flow amount |
| Comparative Example 1 | 0.100 | 1.00 | 0.1000 | 0.100 | — | ◯ |
| Comparative Example 2 | 0.015 | 3.00 | 0.0050 | 0.045 | ◯ | X |
| Comparative Example 3 | 0.080 | 2.00 | 0.0400 | 0.160 | X | ◯ |
| Comparative Example 4 | 0.020 | 0.25 | 0.0800 | 0.005 | ◯ | X |

TABLE 1-continued

| | Air introduction hole | | | | Heater power consumption | Air flow amount |
|---|---|---|---|---|---|---|
| | Thickness (mm) | Width (mm) | Aspect ratio | Cross-sectional area (mm$^2$) | | |
| Example 1 | 0.015 | 1.83 | 0.0082 | 0.028 | ○ | ○ |
| Example 2 | 0.040 | 1.83 | 0.0218 | 0.073 | ○ | ○ |
| Example 3 | 0.080 | 1.83 | 0.0436 | 0.147 | ○ | ○ |
| Example 4 | 0.015 | 1.50 | 0.0100 | 0.023 | ○ | ○ |
| Example 5 | 0.040 | 1.50 | 0.0267 | 0.060 | ○ | ○ |
| Example 6 | 0.080 | 1.50 | 0.0533 | 0.120 | ○ | ○ |
| Example 7 | 0.015 | 1.00 | 0.0150 | 0.015 | ○ | ○ |
| Example 8 | 0.040 | 1.00 | 0.0400 | 0.040 | ○ | ○ |
| Example 9 | 0.080 | 1.00 | 0.0800 | 0.080 | ○ | ○ |

The thickness (height) and width dimensions of the cross section of the air introduction portion 307b respectively correspond to a thickness H1 and a width W1 of the air introduction portion 307b as shown in FIG. 4. The thickness (height) and width dimensions, aspect ratio and area of the cross section of the air introduction portion 307b were varied arbitrarily by adjusting the dimensions of the insulating green sheet, the screen printing dimensions, the dimensions of the insert material etc. during the above manufacturing process.

In each of Examples 1 to 9 and Comparative Examples 1 to 4, the cross section of the sensor element sample had a thickness (height) dimension of 1.2 mm, a width dimension of 3.6 mm, an aspect ratio of 0.333 and an area of 4.32 mm$^2$; and the first electrode region 308a had a height (thickness) dimension of 0.002 mm. The cross section of the sensor element herein refers to that corresponding to the sensor element body 71 (the shielding layer 312, the diffusion limiting member 315, the first solid electrolyte member 309 and the insulation portion 307a) and the heater 73 (the first and second substrates 301 and 303), but excluding the protection layer 17, and taken perpendicular to the longitudinal direction at the position of the first electrode region 308a as mentioned before. The thickness (height) and width dimensions of the cross section of the sensor element sample respectively correspond to a thickness H2 and a width W2 of the sensor element as shown in FIG. 4. The cross section of the sensor element sample was rectangular as shown in FIG. 4 in each of Examples 1 to 9 and Comparative Examples 1 to 4.

The heater power consumption was tested under normal control mode (e.g. target sensor element temperature: 800° C.) and evaluated as "○" when reduced by 20% or more relative to that of Comparative Example 1 and as "X" when reduced by less than 20% relative to that of Comparative Example 1. The heater power consumption test results of the respective sensor element samples are also indicated in TABLE 1.

In each of Examples 1 to 9, the amount of reduction of the heater power consumption was 20% or more so that the heater power consumption test result was "○". The amount of reduction of the heater power consumption was 20% or more so that the heater power consumption test result was "○" in each of Comparative Examples 2 and 4. In Comparative Example 3, however, the amount of reduction of the heater power consumption was less than 20% so that the heater power consumption test result was "X".

It has been shown by the above test results that, in the case where the area of the cross section of the air introduction portion 307b is 0.147 mm$^2$ or smaller, it is possible to reduce the heater power consumption of the sensor element by 20% or more relative to the case where the area of the cross section of the air introduction portion 307b is 0.100 mm$^2$ (Comparative Example 1). It has also been shown by the above test results that it is possible in the case where the aspect ratio of the cross section of the air introduction portion 307b is 0.0800 or smaller to reduce the heater power consumption of the sensor element by 20% or more relative to the case where the aspect ratio of the cross section of the air introduction portion 307b is 0.1000 (Comparative Example 1). Further, it has been shown by the above test results that it is possible in the case where the height dimension of the cross section of the air introduction portion 307b is 0.080 mm or smaller to reduce the heater power consumption of the sensor element by 20% or more relative to the case where the height dimension of the cross section of the air introduction portion 307b is 0.100 mm (Comparative Example 1).

The air flow amount was tested by measuring the amount of air introduced into the air introduction portion 307b according to steady flow differential pressure measurement method as defined by JIS L 1096, and then, judging whether the measured air introduction amount was larger than or equal to an adequate level required for proper gas detection. When the measured air introduction amount was larger than or equal to the adequate level, the air flow amount was evaluated as "○". The air flow amount was evaluated as "X" when the measured air introduction amount was less than the adequate level. The air flow test results of the respective sensor element samples are also indicated in TABLE 1.

In each of Examples 1 to 9, the air flow test result was "○". On the other hand, the air flow test result was "○" in Comparative Examples 1 to 3 and was "X" in Comparative Example 4. In particular, the air introduction amount was larger than or equal to the adequate level in Example 7 where the area of the cross section of the air introduction portion 307b was 0.015 mm$^2$; whereas the air introduction amount was less than the adequate level in Comparative Example 4 where the area of the cross section of the air introduction portion 307b was 0.005 mm$^2$.

It has been shown by the above test results that it is possible to introduce the sufficient amount of air into the air introduction portion 307b for proper gas detection in the case where the area of the cross section of the air introduction portion 307b is 0.015 mm$^2$ or larger.

In Comparative Example 2, the air introduction portion 307b had an aspect ratio of 0.0050, i.e., smaller than 0.0082 and thereby had the difficulty of introducing air under diffusion limited conditions so that the air introduction amount was less than the adequate level although the area of the cross section of the air introduction portion 307b was 0.045 mm$^2$, i.e. larger than or equal to 0.015 mm$^2$.

To sum up, it is preferred that the cross section of the air introduction portion 307b has an aspect ratio of 0.0082 to 0.0800, an area of 0.015 to 0.147 mm² and a thickness (height) dimension of 0.015 to 0.080 mm.

(Measurement Test 2)

The gas sensor element 7 was tested for the heater power consumption and strength by varying the cross section of the gas sensor element 7. Herein, the definitions of the cross section and dimensions of the sensor element are the same as those in Measurement Test 1.

In Measurement Test 2, eleven types of sensor element samples as Examples 11 to 21 of the present invention and five types of sensor element samples as Comparative Examples 11 to 15 were prepared. The thickness (height) and width dimensions, aspect ratio and area of the cross section of the respective sensor element samples are indicated in TABLE 2.

TABLE 2

|  | Sensor element | | | | | |
|---|---|---|---|---|---|---|
|  | Thickness (mm) | Width (mm) | Aspect ratio | Cross-sectional area (mm²) | Heater power consumption | Sensor element strength |
| Comparative Example 11 | 1.13 | 4.00 | 0.281 | 4.50 | — | ○ |
| Comparative Example 12 | 1.50 | 4.00 | 0.375 | 6.00 | X | ○ |
| Comparative Example 13 | 0.4 | 4.00 | 0.100 | 1.60 | ○ | X |
| Comparative Example 14 | 1.00 | 2.00 | 0.500 | 2.00 | X | ○ |
| Comparative Example 15 | 0.30 | 2.00 | 0.150 | 0.60 | ○ | X |
| Example 11 | 1.20 | 3.60 | 0.333 | 4.32 | ○ | ○ |
| Example 12 | 1.00 | 3.60 | 0.278 | 3.60 | ○ | ○ |
| Example 13 | 0.40 | 3.60 | 0.111 | 1.44 | ○ | ○ |
| Example 14 | 1.20 | 3.30 | 0.364 | 3.96 | ○ | ○ |
| Example 15 | 1.00 | 3.30 | 0.303 | 3.30 | ○ | ○ |
| Example 16 | 0.40 | 3.30 | 0.121 | 1.32 | ○ | ○ |
| Example 17 | 1.20 | 3.00 | 0.400 | 3.60 | ○ | ○ |
| Example 18 | 1.00 | 3.00 | 0.333 | 3.00 | ○ | ○ |
| Example 19 | 0.40 | 3.00 | 0.133 | 1.20 | ○ | ○ |
| Example 20 | 0.80 | 2.00 | 0.400 | 1.60 | ○ | ○ |
| Example 21 | 0.40 | 2.00 | 0.200 | 0.80 | ○ | ○ |

The thickness (height) and width dimensions, aspect ratio and area of the cross section of the sensor element sample were varied arbitrarily by adjusting the dimensions of the insulating green sheet, the screen printing dimensions, the dimensions of the insert material etc. during the above manufacturing process.

In each of Examples 11 to 21 and Comparative Examples 11 to 15, the thickness (height) and width dimensions, aspect ratio and area of the cross section of the air introduction portion 307b were the same as those in Example 3 of Measurement Test 1.

The heater power consumption was tested under normal control mode (e.g. target sensor element temperature: 800° C.) and evaluated as "○" when reduced by 20% or more relative to that of Comparative Example 11 and as "X" when reduced by less than 20% relative to that of Comparative Example 11. The heater power consumption test results of the respective sensor element samples are also indicated in TABLE 2.

In each of Examples 11 to 21, the amount of reduction of the heater power consumption was 20% or more so that the heater power consumption test result was "○". The amount of reduction of the heater power consumption was 20% or more so that the heater power consumption test result was "○" in Comparative Examples 13 and 15. In Comparative Examples 12 and 14, however, the amount of reduction of the heater power consumption was less than 20% so that the heater power consumption test result was "X".

It has been shown by the above test results that, in the case where: the aspect ratio of the cross section of the sensor element is 0.400 or smaller; and the area of the cross section of the sensor element is 4.32 mm² or smaller, it is possible to reduce the heater power consumption of the sensor element by 20% or more relative to the case of Comparative Example 11. Further, it has been shown by the above test results that it is possible in the case where the width dimension of the cross section of the sensor element is 3.6 mm or smaller to reduce the heater power consumption of the sensor element by 20% or more relative to the case of Comparative Example 11.

The strength of the sensor element was tested by checking the occurrence or nonoccurrence of breakage such as cracking in a surface of the sensor element during the application of an external force of 40 N/mm² for 10 sec as defined by JIS R1501. When there occurred no breakage in the sensor element, the strength of the sensor element was evaluated as "○". The strength of the sensor element was evaluated as "X" when the breakage occurred in the sensor element. The strength test results of the respective sensor element samples are also indicated in TABLE 2.

In each of Examples 11 to 21, the strength test result was "○". On the other hand, the strength test result was "○" in Comparative Examples 11, 12 and 14 and was "X" in Comparative Examples 13 and 15.

It has been shown by the above test results that it is possible to secure the strength of the sensor element and prevent the occurrence of breakage of the sensor element in the case where: the aspect ratio of the cross section of the sensor element is 0.111 or larger; and the area of the cross section of the sensor element is 0.80 mm² or larger. It has also been shown by the above test results that it is possible in the case where the width dimension of the cross section of the sensor element is 2.0 mm or larger to secure the strength of the sensor element and prevent the occurrence of breakage of the sensor element.

To sum up, it is preferred that the cross section of the gas sensor element 7 has an aspect ratio of 0.111 to 0.400, an area of 0.80 to 4.32 mm$^2$ and a width dimension of 2.0 to 3.6 mm.

1-5. Effects

In the gas sensor element 7 of the air-fuel ratio sensor 1, the air introduction portion 307b has its opening 307c on the rear end side of the insulating layer 307 and communicates with the outside through the opening 307c as mentioned above. The air introduction portion 307b is, when taken in cross section perpendicular to the longitudinal direction at the position of the first electrode region 308a, rectangular in shape.

As is apparent from the test results of TABLE 1, the gas sensor element 7 can prevent an increase in overall heat capacity and obtain improvement in thermal conduction efficiency so as to reduce the power consumption required for heating of the gas sensor element 7 when the cross section of the air introduction portion 307b has an aspect ratio of 0.0800 or smaller and an area of 0.147 mm$^2$ or smaller. The gas sensor element 7 can introduce a sufficient amount of air from the air introduction portion 307b and prevent an insufficient air supply to the first electrode region 308a when the cross section of the air introduction portion 307b has an aspect ratio of 0.0082 or larger and an area of 0.015 mm$^2$ or larger.

Namely, it is possible to not only reduce the power consumption for heating of the gas sensor element 7 but also prevent the insufficient air supply to the first electrode region 308a by controlling the aspect ratio and area of the cross section of the air introduction portion 307b to within the above specific ranges. The gas sensor element 7 (the air-fuel ration sensor 1) is therefore able to provide a sufficient air supply from the air introduction portion 307b to the first electrode region 308a of the detection portion 70 while reducing the power consumption for heating of the gas sensor element 7.

The gas sensor element 7 can also prevent an increase in overall heat capacity and obtain improvement in thermal conduction efficiency so as to reduce the power consumption required for heating of the gas sensor element 7 when the cross section of the air introduction portion 307b has a height dimension of 0.080 mm or smaller.

When the cross section of the air introduction portion 307b has a height dimension of 0.015 mm or larger, the gas sensor element 7 can introduce a sufficient amount of air from the air introduction portion 307b and prevent an insufficient air supply to the first electrode region 308a.

It is namely also possible to reduce the power consumption for heating of the gas sensor element 7 and prevent the insufficient air supply to the first electrode region 308a by controlling the height dimension of the cross section of the air introduction portion 307b to within the above specific range. Thus, the gas sensor element 7 (the air-fuel ration sensor 1) is able to provide a sufficient air supply to the first electrode region 308a of the detection portion 70 while reducing the power consumption for heating of the gas sensor element 7.

Furthermore, the gas sensor element 7 is, when taken in cross section perpendicular to the longitudinal direction at the position of the detection portion 70 (first electrode region 308a), substantially rectangular in shape.

As is apparent from the test results of TABLE 2, the gas sensor element 7 can prevent an increase in overall heat capacity and obtain improvement in thermal conduction efficiency so as to reduce the heater power consumption required for heating of the gas sensor element 7 when the cross section of the gas sensor element 7 has an aspect ratio of 0.400 or smaller and an area of 4.32 mm$^2$ or smaller. The gas sensor element 7 can secure its strength and be prevented from breakage when the cross section of the gas sensor element 7 has an aspect ratio of 0.111 or larger and an area of 0.80 mm$^2$ or larger.

Namely, it is possible to reduce the power consumption for heating of the gas sensor element 7 and ensure the strength of the gas sensor element 7 for prevention of breakage of the gas sensor element 7 by controlling the aspect ratio and area of the cross section of the gas sensor element 7 to within the above specific ranges. The gas sensor element 7 (the air-fuel ratio sensor 1) is therefore able to ensure its strength and prevent breakage while reducing the power consumption for heating of the gas sensor element 7.

The gas sensor element 7 can also prevent an increase in overall heat capacity and obtain improvement in thermal conduction efficiency so as to reduce the power consumption required for heating of the gas sensor element 7 when the cross section of the gas sensor element 7 has a width dimension of 3.6 mm or smaller. The gas sensor element 7 can secure its strength and be prevented from breakage when the cross section of the gas sensor element 7 has a width dimension of 2.0 mm$^2$ or larger.

It is namely also possible to reduce the power consumption for heating of the gas sensor element 7 and ensure the strength of the gas sensor element 7 for prevention of breakage of the gas sensor element 7 by controlling the width dimension of the cross section of the gas sensor element 7 to within the above specific range. The gas sensor element 7 (the air-fuel ratio sensor 1) is thus able to ensure its strength and prevent breakage while reducing the power consumption for heating of the gas sensor element 7.

In the gas sensor element 7, the height (thickness) dimension of the first electrode region 308a is preferably smaller than or equal to a value of subtraction of 0.005 mm from the height dimension of the cross section of the air introduction portion 307b. When the height dimension of the first electrode region 308a is smaller than or equal to the value of subtraction of 0.005 mm from the height dimension of the cross section of the air introduction portion 307b, the gas sensor element 7 can secure a clearance between the first electrode region 308a and an inner surface of the air introduction portion 307b (second substrate 303) facing the first electrode region 308a so as to secure a large area of contact between the first electrode region 308a and the air and provide the first electrode region 308a with reliable sensitivity to the specific gas component (oxygen) in the air.

In the present embodiment, the first electrode region 308a has a height dimension of 0.002 mm. When the height dimension of the first electrode region 308a is 0.002 mm or larger, the gas sensor element 7 can secure the volume of the first electrode region 308a required for reaction with the specific gas component (oxygen) and permit the proper function of the first electrode region 308a so as to generate the electromotive force between the first electrode region 308a and the second electrode region 310a.

Thus, the gas sensor element 7 (the air-fuel ratio sensor 1) is able to ensure the large area of contact between the first electrode region 308a and the air and properly generate the electromotive force between the first electrode region 308a and the second electrode region 310a according to the concentration ratio of the specific gas component (oxygen) by controlling the height dimension of first electrode region 308a to within the above specific range.

1-6. Correspondence to Claims

The correspondence of the above embodiment to claims is as follows: the gas sensor element 7 corresponds to the claimed sensor element; the air-fuel ratio sensor 1 corresponds to the claimed sensor; the first and second electrode regions 308a and 310a correspond to the claimed reference and measurement electrodes, respectively; and the first solid electrolyte member 309 corresponds to the claimed solid electrolyte member.

2. Other Embodiments

Although the present invention has been described with reference to the above specific embodiment, the present invention is not limited to such a specific embodiment. Various modifications and variations can be made to the above embodiment without departing from the scope of the present invention.

The height dimension of the first electrode region 308a (reference electrode) is not limited to 0.002 mm and is set to any arbitrary value within the range larger than or equal to 0.002 mm and smaller than or equal to the value of subtraction of 0.005 mm from the height dimension of the cross section of the air introduction portion 307b.

The air introduction portion 307b is not necessarily a completely hollow space and may be filled with a porous material. In the case where the air introduction portion 307b is filled with a porous material, the porosity of the porous material in the air introduction portion 307b is 10% or more in order to provide a reliable air supply to the first electrode region 308a (reference electrode). In order to introduce a sufficiently large amount of air into the air introduction portion 307b, the porosity of the porous material in the air introduction portion 307b is preferably 30% or more. The porosity of the porous material in the air introduction portion 307b is preferably 50% or more when the gas sensor element 7 is intended for use where it is necessary to supply a large amount of air to the first electrode region 308a (reference electrode). In this case, the cross section of the air introduction portion 307b corresponds to a region of arrangement of the porous material and the first electrode region 308a.

The gas under measurement is not limited to the exhaust gas of the internal combustion engine. Any other gas can be adopted as the gas under measurement. Further, the specific gas component is not limited to oxygen and can be any other gas component.

Although the sensor element is configured as a so-called one-cell type sensor element in the above embodiment, the present invention is not limited to such type of sensor element. The present invention is also applicable to a sensor element with a plurality of cells.

The entire contents of Japanese Patent Application No. 2013-166500 (filed on Aug. 9, 2013) are herein incorporated by reference. The scope of the invention is defined with reference to the following claims.

What is claimed is:

1. A sensor element for detecting a specific gas component in a gas under measurement, the sensor element having a plate shape extending in a longitudinal direction thereof and comprising:
    a detection portion located on a front end side of the sensor element; and
    an air introduction portion adapted as a longitudinal hole having an opening and extending in the longitudinal direction from the opening to a position of the detection portion so as to introduce air thereinto through the opening,
    the detection portion including a measurement electrode exposed to the gas under measurement, a reference electrode arranged in the air introduction portion and a plate-shaped solid electrolyte member held in contact with both of the measurement electrode and the reference electrode,
    wherein a cross section of the air introduction portion taken perpendicular to the longitudinal direction at a position of the reference electrode has an aspect ratio of 0.0082 to 0.0800 and an area of 0.015 to 0.147 mm$^2$.

2. The sensor element according to claim 1, wherein said cross section of the air introduction portion has a height dimension of 0.015 to 0.080 mm in a direction perpendicular to a plate surface of the solid electrolyte member.

3. The sensor element according to claim 1, wherein a cross section of the sensor element taken perpendicular to the longitudinal direction at a position of the detection portion has an aspect ratio of 0.111 to 0.400 and an area of 0.80 to 4.32 mm$^2$.

4. The sensor element according to claim 3, where said cross section of the sensor element has a width dimension of 2.0 to 3.6 in a direction parallel to a plate surface of the sensor element.

5. The sensor element according to claim 1, wherein a height dimension of the reference electrode in a direction perpendicular to a plate surface of the solid electrolyte member is 0.002 mm or larger and is smaller than or equal to a value of subtraction of 0.005 mm from the height dimension of said cross section of the air introduction portion.

6. A sensor, comprising:
    the sensor element according to claim 1; and
    a cylindrical metal shell holding therein the sensor element,
    wherein the sensor element has a heater for heating at least the detection portion.

* * * * *